(12) United States Patent
Madabhushi et al.

(10) Patent No.: US 9,183,350 B2
(45) Date of Patent: Nov. 10, 2015

(54) QUANTITATIVELY CHARACTERIZING DISEASE MORPHOLOGY WITH CELL ORIENTATION ENTROPY

(71) Applicant: Case Western Reserve University, Cleveland, OH (US)

(72) Inventors: Anant Madabhushi, Beachwood, OH (US); George Lee, Parlin, NJ (US); Sahirzeeshan Ali, Houston, TX (US); Rachel Sparks, Seattle, WA (US)

( * ) Notice: Subject to any disclaimer, the term of this patent is extended or adjusted under 35 U.S.C. 154(b) by 86 days.

(21) Appl. No.: 14/226,226

(22) Filed: Mar. 26, 2014

(65) Prior Publication Data

US 2014/0294279 A1    Oct. 2, 2014

Related U.S. Application Data

(60) Provisional application No. 61/806,578, filed on Mar. 29, 2013.

(51) Int. Cl.
| | |
|---|---|
| G06K 9/00 | (2006.01) |
| G06F 19/00 | (2011.01) |
| G06T 7/00 | (2006.01) |
| G01R 33/56 | (2006.01) |
| G06K 9/46 | (2006.01) |
| G06K 9/62 | (2006.01) |

(52) U.S. Cl.
CPC .......... *G06F 19/321* (2013.01); *G01R 33/5608* (2013.01); *G06F 19/3431* (2013.01); *G06K 9/0014* (2013.01); *G06K 9/00147* (2013.01); *G06K 9/4671* (2013.01); *G06K 9/6256* (2013.01); *G06T 7/0014* (2013.01); *G06T 7/0032* (2013.01); *G06T 7/0083* (2013.01); *G06T 7/0087* (2013.01); *G06T 2207/30081* (2013.01)

(58) Field of Classification Search
CPC ................................. G06F 19/00; G06K 9/00
USPC .......................................................... 382/133
See application file for complete search history.

(56) References Cited

U.S. PATENT DOCUMENTS

| | | | | |
|---|---|---|---|---|
| 2010/0298166 | A1* | 11/2010 | Alon et al. | 506/10 |
| 2012/0245045 | A1* | 9/2012 | Kislin et al. | 506/9 |

OTHER PUBLICATIONS

Lee et al., Article: "Cell Orientation Entropy (COrE): Predicting Biochemical Recurrence from Prostate Cancer Tissue Microarrays" from: Medical Image Computing and Computer-Assisted Intervention—MICCAI 2013 16th International Conference, Nagoya, Japan, Sep. 22-26, 2013, Proceedings, Part III, pp. 396-403. Retrieved on Aug. 8, 2015 from Internet Retrieved from: <http://engineering.case.edu/centers/ccipd/sites/ccipd.case.edu/files/publications/MICCAI2013.pdf>.*

Qaiser Mahmood Chaudry, "Improving Cancer Subtype Diagnosis and Grading using Clinical Decision Support System Based on Computer-Aided Tissue Image Analysis", May 2013, Retrieved on Aug. 8, 2015 from Internet from:<https://smartech.gatech.edu/bitstream/handle/1853/47745/chaudry_qaiser_m_201305_phd.pdf>.*

\* cited by examiner

*Primary Examiner* — Gregory F Cunningham (57) ABSTRACT

Apparatus, methods, and other embodiments associated with objectively predicting biochemical recurrence (BCR) with cell orientation entropy (COrE) are described. One example apparatus includes a set of logics that associate directional disorder with a risk of biochemical recurrence in a tissue. A first logic detects a cell in the tissue, segments boundaries of the cell, and calculates a cell direction for the cell. A second logic constructs a localized sparsified subgraph whose nodes represent centroids of the cells, defines pairwise spatial relationships between the cells, and constructs a directional co-occurrence matrix based on the spatial relationships. A third logic derives second order statistical features from the co-occurrence matrix, and produces a BCR risk score as a function of the second order statistical features. The second order statistical features include the entropy of the directional organization of the cells.

25 Claims, 5 Drawing Sheets

Figure 5

QUANTITATIVELY CHARACTERIZING DISEASE MORPHOLOGY WITH CELL ORIENTATION ENTROPY

CROSS REFERENCE TO RELATED APPLICATIONS

This application claims the benefit of U.S. Provisional Application No. 61/806,578 filed on Mar. 29, 2013.

BACKGROUND

Nearly 60,000 patients diagnosed with prostate cancer (CaP) in the United States undergo radical prostatectomy (RP) each year. For 15-40% of these patients, biochemical recurrence (BCR) of the prostate cancer occurs within five years of surgery. Gleason scoring is a pathological grading system based on visual analysis by a pathologist of glandular and nuclear morphology. Gleason scoring is currently regarded as the best biomarker for predicting CaP aggressiveness and long-term post-surgical patient outcome. However, the post-surgical outcome of CaP patients with the same intermediate Gleason scores can vary significantly. For example, patients with a Gleason score of 7 may have a 5-year BCR survival rate as low as 43%. Consequently, detecting BCR shortly after surgery may facilitate determining whether other treatments are necessary, and, if necessary, are initiated. Furthermore, Gleason scoring is subjective and is, therefore, susceptible to considerable inter-reviewer variability. Due to these limitations of Gleason scoring, other post-operative nomograms have been developed for predicting CaP aggressiveness and long-term post-surgical patient outcome.

Conventional methods for determining the extent and severity of cancer have involved a pathologist performing microscopic evaluation of histological images to determine a qualitative grade, e.g. a Gleason score. While conventional qualitative grading has been a valuable prognostic measure of aggressive disease, it suffers from inter-reviewer variability. The development of digital whole slide scanners has allowed the development of quantitative histomorphometry (QH). QH enables automated evaluation of histological tissue, creating accurate and repeatable analysis to attempt to overcome issues with inter-reviewer variability as it relates to quantifying disease appearance.

Conventional computerized QH algorithms for grading and diagnosing cancer have examined features based on co-occurrence matrices for the purpose of automated grading. Jafari-Khouzani et al., Multiwavelet grading of pathological images of prostate. IEEE Trans. On Biomedical Engineering, 50(6) (2003) 697-704. However, these matrices have been based on pixel intensity. Pixel intensity based matrices lack direct biological significance, and are thus less than optimal for diagnosing cancer. Conventional attempts to evaluate prostate histopathology in terms of grading have also looked at color, texture, and structural morphology. Tabesh et al., Multi-feature prostate cancer diagnosis and Gleason grading of histological images. IEEE Trans. on Medical Imaging 26(10) (2007) 1366-1378. However, these conventional methods do not investigate complex spatial relationships between structures.

Graph tessellations of cell nuclei using Voronoi or Delaunay graphs have been used to predict cancer grade. Christens-Barry and Partin, Quantitative grading of tissue and nuclei in prostate cancer for prognosis prediction, Johns Hopkins Apl. Technical Digest, 18:226-233, (1997). These graphs describe the spatial interactions between cell nuclei in the tissue of interest. However, the statistical features derived from Voronoi and Delaunay graphs are derived from fully connected graphs. This connecting of stromal and epithelial nuclei results in features extracted from conventional graphs representing averaged attributes of both stromal and epithelial regions. Unfortunately, such fully connected graphs are not sensitive to local variations in cell organization, and are therefore less than optimal in predicting BCR.

Local cell networks are difficult to quantify due to the variability of the size of the epithelial glands and stromal areas. Different types of cell graphs have been constructed to evaluate breast cancer in an alternative to Voronoi and Delaunay graphs. Bilgen, C. et al., Cell-graph mining for breast tissue modelling and classification. Engineering in Medicine and Biology Society, 2007, IEEE (2007) 5311-5314. While these graphs provide greater local constraints to separate stromal from epithelial regions, conventional graph mining does not include information pertaining to cell morphology.

Thus, while conventional methods for predicting BCR in prostate cancer patients have utilized QH, explored image textures, and employed fully-connected graphs and graph mining to assist in predicting CaP aggressiveness and BCR, conventional methods still suffer from the drawbacks of those techniques.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Conventional systems that rely on Gleason scoring for predicting BCR in CaP patients suffer from inter-reviewer variability which affects the accuracy of their predictions. Example apparatus and methods quantitatively evaluate cellular and nuclear orientation to assess cancer aggressiveness and risk of post-surgical biochemical recurrence in CaP patients. Example apparatus and methods employ an energy based segmentation scheme to detect and segment a set of cells. Example apparatus and methods employ principal component analysis (PCA) to obtain the directionality of the detected cells. Example apparatus and methods construct local cell subgraphs to define pairwise spatial relationships between cells. Example apparatus and methods employ co-occurring cell orientation matrices to derive cell orientation entropy features, also referred to as second-order statistical features, related to the orientations of cells and nuclei in a localized network. Prostate cells and other cells that may be cancerous exhibit different degrees of orientation disorder as a function of malignancy. Therefore, the described apparatus and methods objectively distinguish malignant tissue from benign tissue, and objectively distinguish patients who may or may not experience BCR.

Prostate cancer may be considered to be fundamentally a disease of glandular disorganization. The breakdown in nuclei orientation is related to the aggressiveness of the cancer. Normal benign epithelial cells align themselves with respect to the glands, and thereby display a coherent directionality. In benign or less aggressive prostate cancer, gland orientations within local neighborhoods are similar to each other. Malignant prostate glands lose their capability to orient themselves and consequently display no preferred directionality. In more aggressive disease, gland orientations are dissimilar. As the degree of malignancy increases, and as the degree of aggressiveness of the disease increases, the coherence of the gland orientations within localized regions becomes more disorganized, and may be completely disrupted. This disorganization of gland orientations varies as a function of malignancy. Furthermore, this disorientation of glands results in a more chaotic organization and orientation of the surrounding epithelial cells. Such disorientation is also present in cancers other than CaP. Example systems and methods quantify cell orientation, use subgraphs to construct local cell networks, and derive cell entropy orientation features from co-occurrence matrices that capture certain signatures within the local neighborhoods across the image.

Quantitative histomorphometry applies advanced computational image analysis to reproducibly and automatically describe the appearance of disease in histological tissue. Conventionally, QH features have been modelled after pathological Gleason grades. Gleason scoring is a qualitative system in which a pathologist uses tissue morphology to assess CaP aggressiveness. A pathologist may use morphological descriptors such as gland size and perimeter ratio to assign a Gleason score, where a lower score (e.g., 3) is associated with more favorable longer term prognosis, and a higher score (e.g., 8-10) is associated with a less favorable longer term prognosis. Conventional Gleason scoring therefore suffers from inter-reviewer variability, especially around intermediate Gleason scores (e.g., 7). Different patients with identical intermediate Gleason scores may exhibit substantially different longer term outcomes. QH attempts to create accurate and repeatable analysis to overcome these inter-reviewer variability problems. However, the reliance on Gleason scoring retains the problems of Gleason scoring, in part because conventional Gleason scoring, even applied to QH, does not take into account cell orientation or nuclei orientation. Example apparatus and methods facilitate distinguishing outcomes for patients with identical Gleason scores.

QH tissue architecture has been modeled using graph networks to characterize the spatial arrangement of nuclei and glands. Voronoi and Delaunay features have been used to describe the architecture of various structures in CaP histology. For example, minimum spanning trees, in addition to Voronoi and Delaunay features, have been shown to be strong predictors of Gleason score. Conventional implementations of Voronoi and Delaunay features with minimum spanning trees, are, however, derived from fully connected graphs. Fully connected graphs are not sensitive to local cellular orientation. Nuclei embedded within stromal and epithelial regions are connected in fully connected graphs. The graph edges in these fully connected graphs will traverse the epithelial-stromal interfaces and regions. Statistics derived from fully connected graphs are extracted across nuclei epithelial and stomal regions, rather than within clustered cell networks. Consequently, the features extracted from conventional fully connected graphs represent averaged attributes of both stromal and epithelial architecture, and are therefore less than optimal in predicting BCR and distinguishing cancerous from non-cancerous tissue.

Example apparatus and methods individually segment cell boundaries from TMA core images. A direction is assigned to the detected cells. The assigned direction represents the dominant orientation of the cell based off the major axis of the cell. A subgraph is then constructed where the nodes of the subgraph represent the centroids of cell nuclei. The subgraph links together cells proximal to each other into a localized cell network. The subgraph of the localized cell network characterizes the local cell arrangement. Unlike conventional implementations of Voronoi and Delaunay features with minimum spanning trees, the subgraph of the localized cell network prevents subgraph edges from traversing heterogeneous tissue regions such as stroma and epithelium. Since the subgraphs are localized and limited to the epithelial regions, the contributions from the stromal regions are minimized.

Example apparatus and methods employ a co-occurrence matrix to capture second-order statistics of cell orientations within localized cell networks in the TMA core image. A co-occurrence matrix captures the frequency with which orientations of two cells proximal to each other co-occur. Co-occurrence features, including entropy, are extracted from the co-occurrence matrix associated with localized cell networks. Localized cell networks may also be referred to as neighborhoods. The extracted co-occurrence features capture the degree to which cell orientations are similar or divergent to each other within the localized cell network. A localized cell network, or neighborhood, with a high entropy value would reflect a high degree of disorder among cell orientations. A low entropy value indicates that the cell directions are likely to be aligned roughly in the same direction within the neighborhood or localized network. The level of malignancy or aggressiveness is related to the level of disorder among cell orientations.

Example apparatus and methods employ an energy based segmentation scheme to detect and segment cells. The energy based segmentation scheme detects and segments a set of cells $\gamma_i$, $p \in \{1, 2, \ldots, n\}$ where n is the total number of nuclei found. The segmentation scheme is a synergy of boundary and region-based active contour models that incorporates shape priors in a level set formulation with automated initialization based on watershed. The term "shape priors" is used herein as a term of art in the computer vision field. For example, a shape prior model may be constructed from a training set of shapes using statistical methods. The shape prior may provide information to the detection and segmentation scheme about shapes that are likely to be encountered in histological images. Integrating prior shape knowledge of the objects being segmented in the form of shape priors with active contours facilitates simultaneous registration and segmentation. In one embodiment, the object of interest from which the shape prior is constructed is a prostate cell nuclei. In another embodiment the object of interest may be a prostate cell. The shape prior may be constructed based on other objects of interest, and is not limited to prostate cells or prostate cell nuclei.

Example apparatus and methods employ an energy functional of the active contour to detect cells and segment cell boundaries. The energy functional of the active contour includes at least three terms: a shape term, a boundary term, and a region term. The combined shape, boundary, and region-based functional is formulated as:

$$F = \beta_s \int_\Omega (\phi(x)-\psi(x))^2 |\nabla\phi|\delta(\phi)dx + \beta_r \int_\Omega \Theta_{in} H_\psi dx + \int_\Omega \Theta_{out} H_{-\psi} dx$$

where $\beta_s, \beta_r > 0$ are arbitrary positive constants that balance contributions of the boundary based shape prior and the region term. $\{\phi\}$ is a level set function. $\psi$ is the shape prior. $\delta(\cdot)$ is the Dirac delta function. $\delta(\phi)$ is the contour measure on $\{\phi=0\}$. $H(\cdot)$ is the Heaviside function. $\Theta_r = |I-u_r|^2 + \mu|\nabla u_r|^2$ where $r\in\{in,out\}$. $u_r$ where $r\in\{in,out\}$ are partitioned foreground and background regions. $\Omega$ is a bounded open set in $\mathbb{R}^2$.

In the combined shape, boundary, and region-based functional, the first term, or shape term, is the prior shape term modeled on the prostate nuclei. The shape term thereby constrains the deformation achievable by the active contour. It should be noted that the first term may be written in terms of at least rotation, translation, or a scaling factor. The second term, or boundary term, is a boundary based term that detects the nuclear boundaries from image gradients. In one embodiment, the first term is combined with the second term, and the combined terms are expressed as $\beta_s \int_\Omega (\phi(x)-\psi(x))^2 |\nabla\phi|\delta(\phi) dx$. In one embodiment, $\beta_s \int_\Omega (\phi(x)-\psi(x))^2 |\nabla\phi|\delta(\phi)dx$ is referred to as the shape plus boundary force. The third term, or region term, drives the shape prior and the contour towards the nuclear boundary based on region statistics. The region term in the form of a region force is expressed as $\beta_r \int_\Omega \Theta_{in} H_\psi dx + \int_\Omega \Theta_{out} H_{-\psi} dx$.

Example apparatus and methods automatically initialize the active contour. Automated initialization of the active contour is based on the watershed principle for image segmentation. The watershed transform may be considered as a region-based segmentation approach that is applied to segment touching objects. Another embodiment may employ a different detection and segmentation scheme. For example, one embodiment may employ automatic region growing to detect and segment cells, instead of or in addition to an energy functional of the active contour.

Example apparatus and methods perform principal component analysis (PCA) to determine the directionality of cells. To determine the directionality of a cell $\gamma_i$, example apparatus and methods perform PCA on a set of cell boundary points $[x_i, y_i]$ to obtain the principal components $Z=[z_1, z_2]$. The first principal component $z_1$ describes the directionality of the cell in the form of the major axis $z_1 = \langle z_1^x, z_1^y \rangle$. The major axis is the axis along which the greatest variance occurs in the nuclear boundary. Example apparatus and methods then convert the principal axis $z_1$ to an angle $\bar\theta(\gamma_i) \in [0°, 180°]$ counterclockwise from the vector $\langle 1, 0 \rangle$ by $$\bar\theta(\gamma_i) = \frac{180°}{\pi} \arctan\left(\frac{z_1^y}{z_1^x}\right).$$

Example apparatus and methods define pairwise spatial relationships between cells using localized subgraphs. A subgraph $G=\{V,E\}$ is defined where V represents the set of n nuclear centroids $\gamma_i, \gamma_j \in V$. Nodes are defined as $i,j \in \{1, 2, \ldots, n\}$. E represents the set of edges that connect the nodes in the subgraph G. The edges between the pairs of nodes $\gamma_i, \gamma_j$ are set as a probabilistic decaying function $$E=\{(i,j): r < d(i,j)^{-\alpha}, \forall \gamma_i, \gamma_j \in V\}$$

where $d(i,j)$ represents the Euclidean distance between nodes $\gamma_i$ and $\gamma_j$. The density of the graph is controlled by $\alpha \geq 0$. $\alpha$ approaching 0 indicates a high probability of connecting nodes while $\alpha$ approaching infinity indicates a low probability of connecting nodes. $r \in [0, 1]$ is an empirically determined edge threshold. In one embodiment, $r \in [0, 1]$ may be generated by a random number generator.

Example apparatus and methods derive cell orientation entropy (COrE) features from the cell directions. The objects of interest in calculating the COrE features are the cell directions given by a discretization of the angles $\bar\theta(\gamma_i)$ such that $$\bar\theta(\gamma_i) = \omega * \text{ceiling}\left(\frac{\theta}{\omega}\right)$$

where $\omega$ is a discretization factor. As a discretization factor, $\omega$ defines a bin width, so that cell orientations within the bin width are considered to be the same orientation. In one embodiment, $\omega$ may be assigned a value of 5, in which case angles would be binned in discrete groups of 5 degrees. In other embodiments, other discretization factors $\omega$ could be used. Neighborhoods for cells are defined by the local cell subgraphs G. For cells $\gamma_i \in V$ a neighborhood $N_i$ is defined to include all $\gamma_j \in V$ where a path between $\gamma_i$ and $\gamma_j$ exists in the subgraph G. Recall that edges in the subgraph G are set by a probabilistic decaying function. Thus, the subgraph will not be a fully connected graph, in contrast to conventional methods. Furthermore, depending on the controlling factor $\alpha \geq 0$, the subgraph may be more or less connected, depending on the value assigned to $\alpha$.

Example apparatus and methods construct an N×N co-occurrence matrix C to capture angle pairs that co-occur in the neighborhoods $N_i$, N being an integer. The co-occurrence matrix C is defined such that for the neighborhoods $N_i$.

$$C_{N_i}(a,b) = \sum_{\gamma_i,\gamma_j}^{N_i} \sum_{a,b=1}^{N} \begin{cases} 1, & \text{if } \theta(\gamma_i)=\alpha \text{ and } \theta(\gamma_j)=\beta \\ 0, & \text{otherwise} \end{cases}$$

where $$N = \frac{180}{\omega}.$$

In one embodiment, N represents the number of discrete angular bins.

Example apparatus and methods extract up to 13 second order statistical features from the co-occurrence matrices $C_{N_i}(a,b)$. The second order statistical features include contrast energy, contrast inverse moment, contrast average, contrast variance, contrast entropy, intensity average, intensity variance, intensity entropy, entropy, energy, correlation, and information measure. Mean, standard deviation, and range of $\Theta$ across $N_i$ represent the set of COrE features. In one embodiment, the co-occurrence matrices may be summed to provide a visual interpretation of cell disorder. For example, a summation of co-occurrence matrices may be visualized in a heatmap, and show brighter co-occurrence values in off-diagonal cells. In this example, brighter values indicate higher co-occurrence of nuclei of differing orientations, and darker values indicate lower co-occurrence of nuclei of differing orientations.

In example apparatus and methods, entropy may be defined as $\Sigma_{a,b} -C(a,b)\log(C(a,b)))$. Energy may be defined as $\Sigma_{a,b} C(a,b)^2$. Correlation may be defined as $$\sum_{a,b} \frac{(a-\mu a)(b-\mu b)C(a,b)}{\sigma_a, \sigma_b}.$$

Contrast (variance) may be defined as $\Sigma_{a,b}|a-b|^2 C(a,b)$. In other embodiments, other second-order statistical features may be extracted from the co-occurrence matrices. By using second-order statistical features derived from the co-occurrence matrices, example apparatus and methods offer a statistically significant improvement in distinguishing cancerous from non-cancerous tissue regions, and in predicting BCR, compared to conventional methods.

Example apparatus and methods selectively differentiate cancerous tissue regions from non-cancerous tissue regions, based on the COrE features. In one example, the cancerous tissue region and the non-cancerous tissue region are differentiated as a function of the disorganization of the cell orientation. A level of disorganization below a disorganization threshold indicates a non-cancerous tissue region, while a disorganization above the disorganization threshold indicates a cancerous tissue region. Example apparatus and methods also calculate a BCR recurrence score based on the COrE features. In one example, a BCR recurrence score is calculated as a function of the disorganization of the cell orientation, as expressed by the COrE features. A level of disorganization below a disorganization threshold results in a low probability of BCR, while a disorganization above the disorganization threshold results in a higher probability of BCR.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
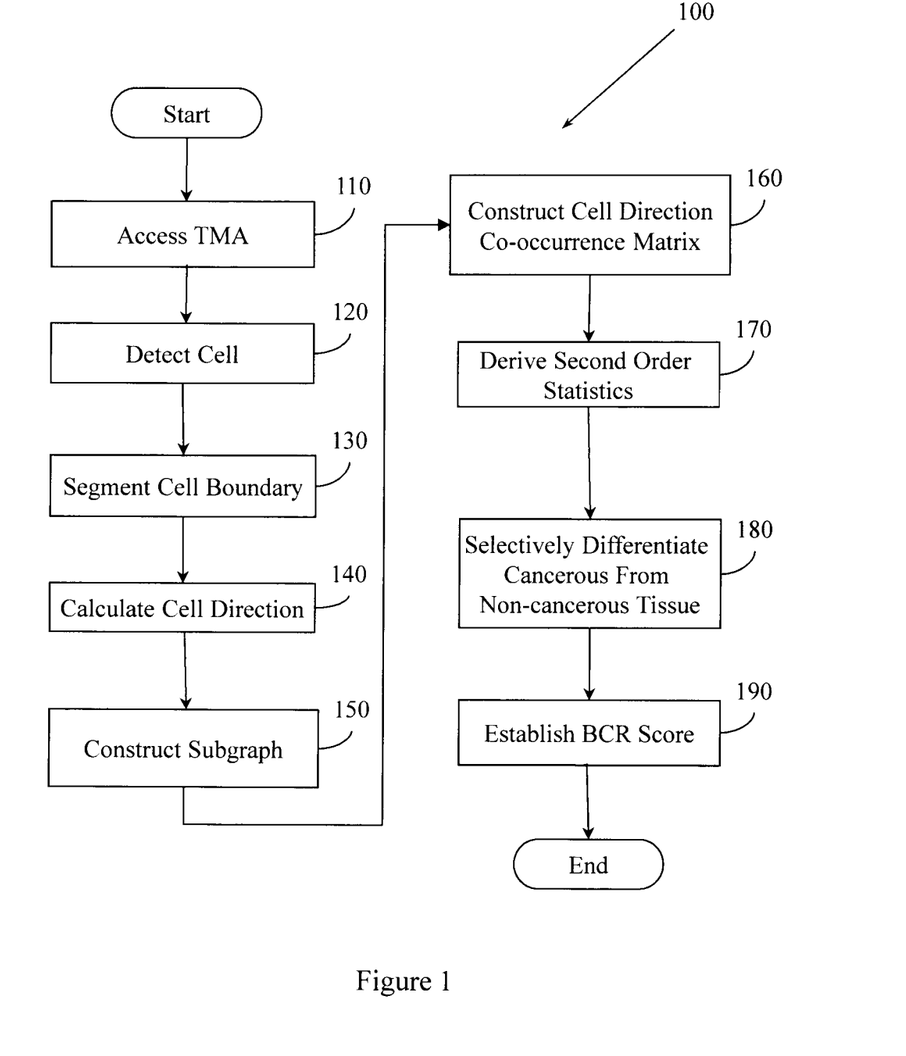
FIG. 1 illustrates an example method of associating cell orientation disorder with malignancy and risk of post-surgical biochemical recurrence (BCR) in a prostate cancer (CaP) patient.

FIG. 1 illustrates a computerized method 100 of associating cellular nuclei orientation entropy with malignancy and risk of post-surgical biochemical recurrence (BCR) in a prostate cancer (CaP) patient. Method 100 includes, at 110, accessing a tissue microarray (TMA) core image of a section of a prostate demonstrating pathology associated with CaP in a patient. Accessing the TMA core may include, for example, acquiring data from a medical imaging apparatus, receiving data via a computer network, receiving data through a function call, or other computer based operation. In one embodiment, prostate excised after radical prostatectomy may be sectioned, stained, and digitized using a scanner configured to operate with tissue microarrays. In one embodiment, the TMA is constructed using four replicate 0.66 mm core tissue samples from the cancer patient. In different embodiments, the TMA may be constructed using a different number of core tissue samples and different sized tissue samples, and the tissue micro array may be digitized at different resolutions.

Method 100 also includes, at 120, detecting a cell in a region of interest in the TMA core image. In one embodiment, detecting the cell is based on an energy functional of an active contour. In another embodiment, detecting a cell in the region of interest may include automatic region growing. One method of automatic region growing is described in US 2011-0243417 A1. Other embodiments may employ other methods of detecting a cell in a region of interest in the TMA core image.

Method 100 also includes, at 130, segmenting the boundary of the cell detected in the TMA core into a set of cell boundary points. Segmenting the boundary of the cell may be based on an energy functional of an active contour. In another embodiment, segmenting is performed by automatic region-growing. Segmentation by automatic region growing may be performed using the luminance channel in Commission internationale de l'éclairage L*a*b* (CIELAB) color space. In another embodiment, color spaces other than CIELAB that include a luminance channel may be used.

Method 100 also includes, at 140, calculating a cell orientation by associating a direction with the cell. The cell orientation indicates the dominant orientation of the cell, and the cell orientation may be based on the major axis of the gland. In one embodiment, the dominant orientation of the cell is obtained through PCA of the set of cell boundary points. The first principal component describes the directionality of the cell in the form of the major axis. The greatest variance in the cell boundary occurs along the major axis. In another embodiment, the dominant orientation of the cell may be obtained through other methods. In one embodiment, method 100 converts the major axis to an angle counterclockwise from a positive horizontal axis. For example, method 100 may convert the major axis to an angle $\theta(\gamma_p) \in [0°, 180°]$ counterclockwise from the vector <1, 0>. In another embodiment, the angle $\theta(\gamma_p)$ may be computed from a different vector, in a different direction, or within a different co-ordinate system. In one embodiment, method 100 also includes discretizing gland orientations. For example, the angle $\theta(\gamma_p)$ may be discretized such that $$\bar{\theta}(\gamma_p) = \omega * \text{floor}\left(\frac{\theta}{\omega}\right)$$

where ω is a discretization factor. In another embodiment, the discretization factor ω may be 10, which would discretize the angles into bins of ten degrees. In another embodiment, the discretization factor ω may be a value other than 10, which would discretize the angles into different sized bins.

Method 100 also includes, at 150, constructing a subgraph of a localized cell network within the region of interest. Constructing the subgraph includes linking individual cells located proximal to each other into the localized cell network, where the nodes of the subgraph represent individual cell nuclei centroids. The edges of the subgraph are defined between pairs of cells by a probabilistic decaying function. Constructing a localized subgraph facilitates characterization of local cell arrangement, and prevents subgraph edges from traversing heterogeneous tissue regions including stroma and epithelium, thereby improving on conventional methods. Preventing graph edges from traversing heterogeneous tissue regions including stroma and epithelium eliminates noise from the regions that separate the glandular regions. In one embodiment, the subgraph is a sparsified graph. The sparsified graph defines a pairwise spatial relationship between the cells. In one embodiment, the probabilistic decaying function is a probabilistic decaying function of the Euclidean distance between cell centroids. In another embodiment, a different probabilistic decaying function may be used to define the edges of the subgraph. In one embodiment, the density of the subgraph is controlled by a randomly generated value $\alpha$, where $\alpha$ is a real number. $\alpha$ may range from 0 through infinity, where 0 represents a high probability of connecting nodes, and infinity represents a low probability of connecting nodes.

Method 100 also includes, at 160, constructing a cellular orientation co-occurrence matrix. In one embodiment, elements of the cellular orientation co-occurrence matrix include cell direction pairs. The cell direction pairs are defined by the subgraph. The cellular orientation co-occurrence matrix aggregates co-occurring cell directions based, at least in part, on the frequency with which orientations of two individual cells located proximal to each other co-occur. In contrast to conventional systems that employ co-occurrence matrices and which analyze first-order statistics based primarily on texture, the COrE features implicitly capture the cyclical properties of cell orientation. COrE features introduce more biological information compared to conventional texture features, which focus only on grayscale pixel intensity. Consequently, higher classification accuracy is achieved compared to conventional methods. When used in combination with conventional methods, method 100 employing COrE features results in classification accuracies of at least 83.6%. In contrast, conventional methods of classification, using nuclear architecture based features, Voronoi graphs, Delaunay graphs, and nuclear morphology, achieve at best a 79.9% classification accuracy.

Method 100 also includes, at 170, deriving second-order statistics of cell orientations in the localized cell networks in the TMA image. In one embodiment, the second-order statistics include entropy, homogeneity, energy, correlation, contrast energy, contrast inverse moment, contrast average, contrast variance, contrast entropy, intensity average, intensity variance, or intensity entropy. In another embodiment, other second-order statistics may be derived. Different combinations of second-order statistics may be employed in different embodiments.

Method 100 also includes, at 180, selectively differentiating a cancerous tissue region from a non-cancerous tissue region in the image based, at least in part, on the second-order statistics. In one embodiment, selectively differentiating a cancerous tissue region from a non-cancerous tissue region is a function of the disorganization of the cell orientation. For example, a level of disorganization below a disorganization threshold indicates a non-cancerous tissue region, while a disorganization level above the disorganization threshold indicates a cancerous tissue region. The disorganization level may be represented numerically, visually, or in other ways. In one example, a heat map of the co-occurrence matrices of the region of interest is generated, and areas of similar disorganization are displayed by similar colors. The colors may pertain to cell orientations from 0° to 180°. For example, the heat map may denote the frequency with which cells of different directionalities co-occur in each neighborhood. A first color may indicate low co-occurrence and a second color may indicate high co-occurrence. In another embodiment, method 100 may include summing the co-occurrence matrices to provide a visual interpretation of the cell orientation disorder. For example, the brightness of a co-occurrence value may vary directly with co-occurrence of nuclei of differing orientations. The cell orientation disorder may be displayed with graphical visual representations other than brightness and color, including size, shape, direction, and other parameters.

Method 100 also includes, at 190, establishing a BCR score for the patient based, at least in part, on the second-order statistics. In one embodiment, the mean, standard deviation, and range of $\Theta$ across all $N_i$ are calculated, yielding the set of COrE features. The set of COrE features may be used to train a classifier to distinguish between categories of interest. The classifier may then assign each region of interest into classes. In one embodiment, the classifier is a random forest classifier. In other embodiments, other types of classifier may be used. Predicting BCR in CaP patients using method 100 in combination with conventional methods results in a statistically significant improvement in classification accuracy over conventional methods alone.

While FIG. 1 illustrates various actions occurring in serial, it is to be appreciated that various actions illustrated in FIG. 1 could occur substantially in parallel. By way of illustration, a first process could segment individual cell boundaries, a second process could produce a cell orientation, and a third process could construct a subgraph of a localized cell network. While three processes are described, it is to be appreciated that a greater or lesser number of processes could be employed and that lightweight processes, regular processes, threads, and other approaches could be employed.

Figure 2:
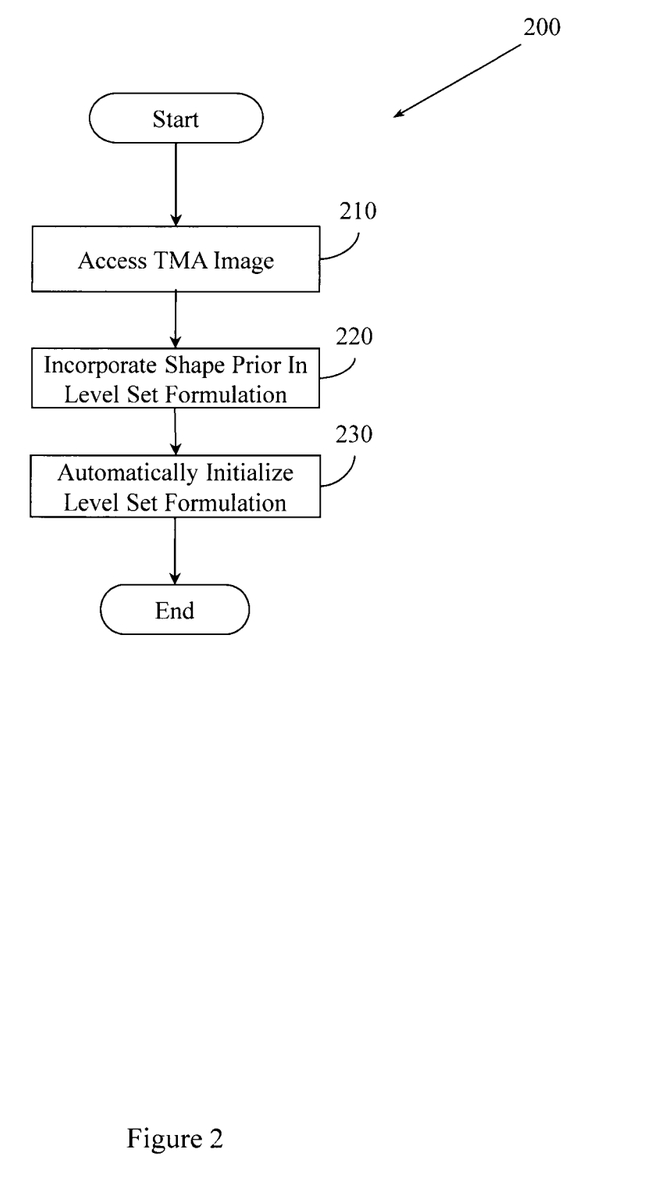
FIG. 2 illustrates an example method of detecting a cell and segmenting an individual cell boundary.

FIG. 2 illustrates an embodiment of a computerized method 200 for detecting a cell and segmenting an individual cell boundary. Method 200 employs an energy functional of an active contour. Method 200 includes, at 210, accessing a tissue microarray image of a section of a prostate demonstrating pathology associated with CaP in a patient. Accessing the TMA may include, for example, acquiring data from a medical imaging apparatus, receiving data via a computer network, receiving data through a function call, or other computer based operation. In another embodiment, the TMA image may be of tissue section other than a section of prostate. For example, the TMA image may be of a section of breast tissue. Method 200 also includes, at 220, controlling the computer to incorporate a shape prior in a level set function. Integrating prior shape knowledge of the objects being segmented in the form of shape priors with active contours facilitates detection and segmentation. In one embodiment, the object of interest of the shape prior is a prostate cell nuclei. In another embodiment, the object of interest may be the cell nuclei other than prostate cell nuclei.

Method 200 also includes, at 230, controlling the computer to automatically initialize the level set formulation. In one embodiment, the initialization is based on a watershed transform. In another embodiment, other transforms may be employed to initialize the level set formulation.

In one embodiment of method 200, the energy functional of an active contour includes a prior shape term. The prior shape term may be modelled on a cell nuclei. The prior shape term constrains deformation achieved by the active contour. The energy functional also includes a boundary-based term. The boundary-based term detects nuclei boundaries from image gradients. The energy functional also contains a region term. The region term drives the shape prior and contour towards the nuclear boundary based on region statistics. In one embodiment, method 200 also includes controlling the computer to combine the prior shape term and boundary-based term to form a shape-plus-boundary force expressed in the energy functional of an active contour. The shape-plus-boundary force is described by $\beta_s \int_\Omega (\phi(x) - \psi(x))^2 |\nabla \phi| \delta(\phi) dx$, where $\beta_s > 0$ is an arbitrary positive constant that balances contributions of the boundary-based shape prior term, where $\{\phi\}$ is a level set function, where $\psi$ is the shape prior, where $\delta(\cdot)$ is the Dirac delta function, where $\delta(\phi)$ is the contour measure on $\{\phi=0\}$, and where $\Omega$ is a bounded open set in $\mathbb{R}^2$. In one embodiment, method 200 also includes the region term expressed in the energy functional of an active contour as a region force. The region force is expressed as $\beta_r \int_\Omega \Theta_{in} H_\psi dx + \int_\Omega \Theta_{out} H_{-\psi} dx$, where $\beta_r > 0$ is an arbitrary positive constant that balances contributions of the region term, where $\psi$ is the shape prior, where $H(\cdot)$ is the Heaviside function, where $\Theta_r = |I - u_r|^2 + \mu |\nabla u_r|^2$, where $r \in \{in, out\}$, where $u_r$ such that $r \in \{in, out\}$ are partitioned foreground and background regions, and where $\Omega$ is a bounded open set in $\mathbb{R}^2$.

Figure 3:
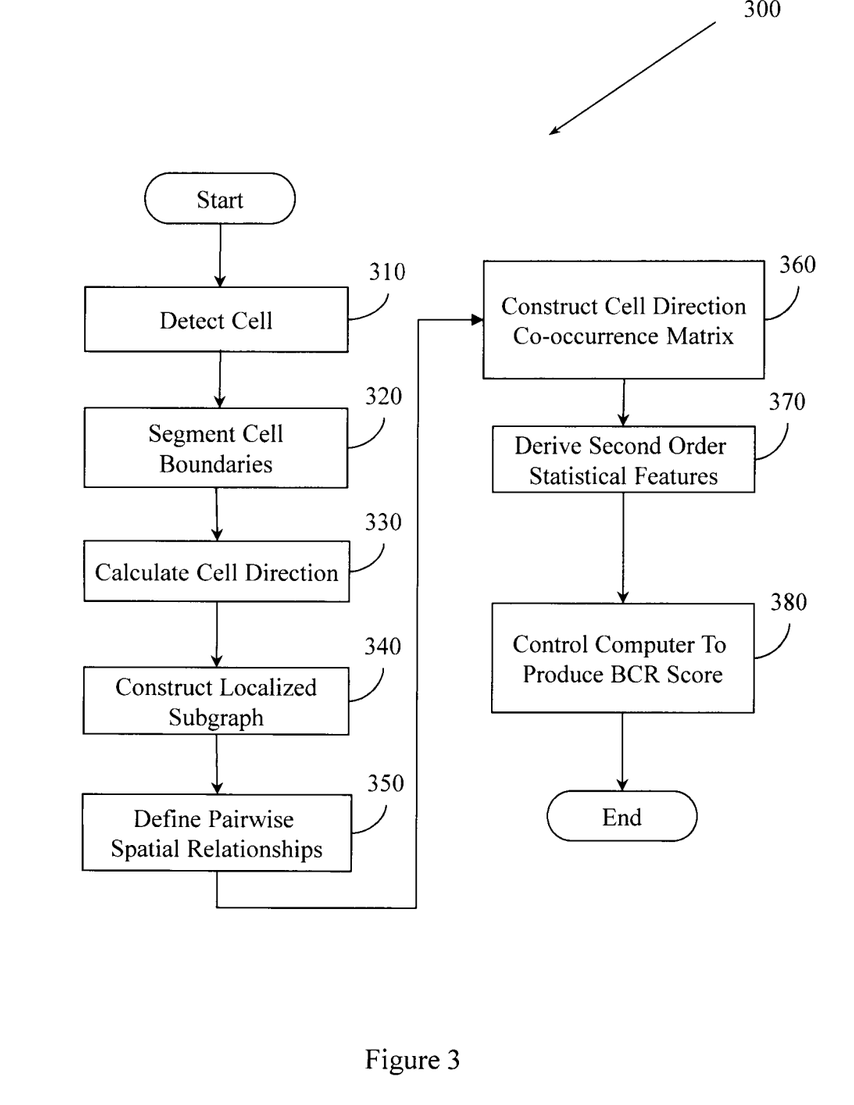
FIG. 3 illustrates an example method of controlling a computer to provide a BCR score for a cancer patient.

FIG. 3 illustrates a method 300 for controlling a computer to provide a biochemical recurrence (BCR) score for a cancer patient. Method 300 includes, at 310, detecting a cell in a region of interest in a TMA image associated with the cancer patient. Method 300 also includes, at 320, segmenting cell boundaries of the cell into a set of cell boundaries. In one embodiment, an energy functional of an active contour is used to detect the cell and segment the cell boundaries. The energy functional may include a prior shape term, a boundary-based term, and a region term. In another embodiment, detecting the cell and segmenting the cell boundaries may be accomplished with a technique other than an energy functional of an active contour.

Method 300 also includes, at 330, calculating a cell direction, based, at least in part, on members of the set of cell boundaries. In one embodiment, the cell direction is calculated from a PCA of the set of cell boundaries.

Method 300 also includes, at 340, constructing a localized subgraph of a cell network in the region of interest of the TMA. The localized subgraph is constructed by linking cells detected in the region of interest and located proximal to each other. The nodes of the subgraph represent individual cell nuclei centroids. In one embodiment, the localized subgraph is a cluster graph. The nodes of the cluster graph may represent cell centroids. In another embodiment, the nodes of the cluster graph may represent cell nuclei centroids. Method 300 also includes, at 350, defining pairwise spatial relationships between two or more cells in the subgraph. In one embodiment, the edges of the localized subgraph between at least one pair of cells are defined by a probabilistic decaying function. The probabilistic decaying function minimizes the contributions of the stromal regions by preventing subgraph edges from traversing heterogeneous tissues including stroma and epithelium. In one embodiment, the probabilistic decaying function is a probabilistic decaying function of the Euclidean distance between cell nuclei centroids.

Method 300 may also include, at 350, varying the density of the subgraph by varying the probability of connecting nodes. In another embodiment, the edges of the subgraph may be defined by a different probabilistic decaying function.

Method 300 also includes, at 360, constructing a cell direction co-occurrence matrix. The cell direction co-occurrence matrix is based, at least in part, on the pairwise spatial relationships. Method 300 also includes, at 370, deriving second order statistical features, which may be referred to as COrE features, from the cell direction co-occurrence matrix. In one embodiment, the second order statistical features include at least one of entropy, contrast, energy, and correlation. In one embodiment, entropy is defined as $\Sigma_{a,b} - C(a,b)\log(C(a,b))$. In the entropy definition a is a direction of a first cell in a pair of cells in the localized subgraph, b is a direction of a second cell in the pair of cells, and C is the cell direction co-occurrence matrix. The cell direction co-occurrence matrix is a N×N co-occurrence matrix. In one embodiment, contrast is defined as $\Sigma_{a,b} |a-b|^2 C(a,b)$. In the contrast definition a is a direction of a first cell in a pair of cells in the localized subgraph, b is a direction of a second cell in the pair of cells, and C is the cell direction co-occurrence matrix. The cell direction co-occurrence matrix is a N×N co-occurrence matrix, N being an integer. Contrast may also be referred to as contrast (variance). In one embodiment, energy is defined as $\Sigma_{a,b} C(a,b)^2$. In the energy definition, a is a direction of a first cell in a pair of cells in the localized subgraph, b is a direction of a second cell in the pair of cells, and C is the cell direction co-occurrence matrix. Once again, the cell direction co-occurrence matrix is a N×N co-occurrence matrix. In one embodiment, correlation is defined as $$\sum_{a,b} \frac{(a-\mu a)(b-\mu b) C(a,b)}{\sigma_a, \sigma_b}.$$

In the correlation definition, a is a direction of a first cell in a pair of cells in the localized subgraph, b is a direction of a second cell in the pair of cells, and C is the cell direction co-occurrence matrix. The cell direction co-occurrence matrix is a N×N co-occurrence matrix.

Method 300 also includes, at 380, controlling the computer to produce a BCR recurrence score based, at least in part, on the second order statistical features derived from the cell direction co-occurrence matrix. In one embodiment, summed cell direction co-occurrence matrices denote the frequency with which two cells of two directionalities co-occur. In another embodiment, a color map of the cell subgraphs corresponds to the average intensity in each neighborhood. Producing an objective BCR score based, at least in part, on the second order statistical features derived from the cell direction co-occurrence matrix combined with conventional methods provides a statistically significant improvement in accuracy compared to conventional methods alone.

Figure 4:
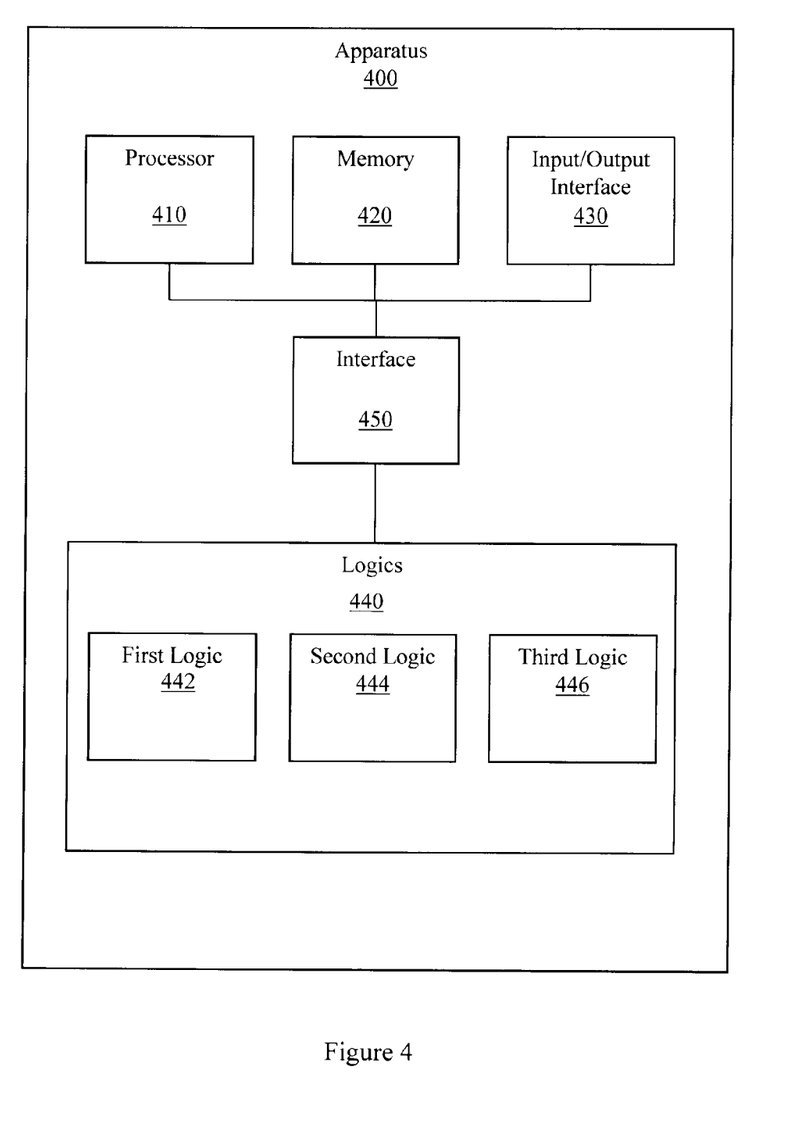
FIG. 4 illustrates an example apparatus that generates a BCR score for a patient based on directional disorder.

FIG. 4 illustrates an example apparatus 400 for objectively predicting biochemical recurrence with cell orientation entropy. In one embodiment, the cells may be prostate cells. In another embodiment, the cells may be other glandular cells. Apparatus 400 may objectively predict biochemical recurrence with cell orientation entropy cellular tissues in which cancer of the cellular tissue causes disorganization of the cell orientations within the tissue. Apparatus 400 includes a processor 410, a memory 420, an input/output interface 430, a set of logics 440, and an interface 450. Interface 450 connects the processor 410, the memory 420, the input/output interface 430, and the set of logics 440.

The set of logics 440 associates directional disorder with a risk of BCR in a region of interest in the cancerous tissue. The set of logics includes a first logic 442. First logic 442 detects a cell in the region of interest. First logic 442 segments boundaries of the cell. In one embodiment, first logic 442 segments boundaries using an energy functional of an active contour. In another embodiment, first logic 442 segments boundaries of the cell using automatic region growing.

The set of logics 440 includes a second logic 444 that constructs a sparsified localized subgraph from the detected cells and segmented cell boundaries. Second logic 444 defines pairwise spatial relationships between the cells in the subgraph. In one embodiment, second logic 444 uses a probabilistic decaying function to set the edges between the nodes of the subgraph. Second logic 444 constructs a cell direction co-occurrence matrix based, at least in part, on the pairwise spatial relationships. In one embodiment, the nodes of the sparsified local subgraph represent the centroids of the cell nuclei.

The set of logics 440 also includes a third logic 446 that derives COrE features, or second-order statistical features, from the directional co-occurrence matrix. In one embodiment, the COrE features include at least one of entropy, energy, homogeneity, and correlation. In other embodiments, logic 446 may derive other additional COrE features, including but not limited to, contrast energy, contrast inverse moment, contrast average, contrast variance, contrast entropy, intensity average, intensity variance, or intensity entropy. Third logic 446 also produces a BCR risk score based, at least in part, on the second-order statistical features.

Figure 5:
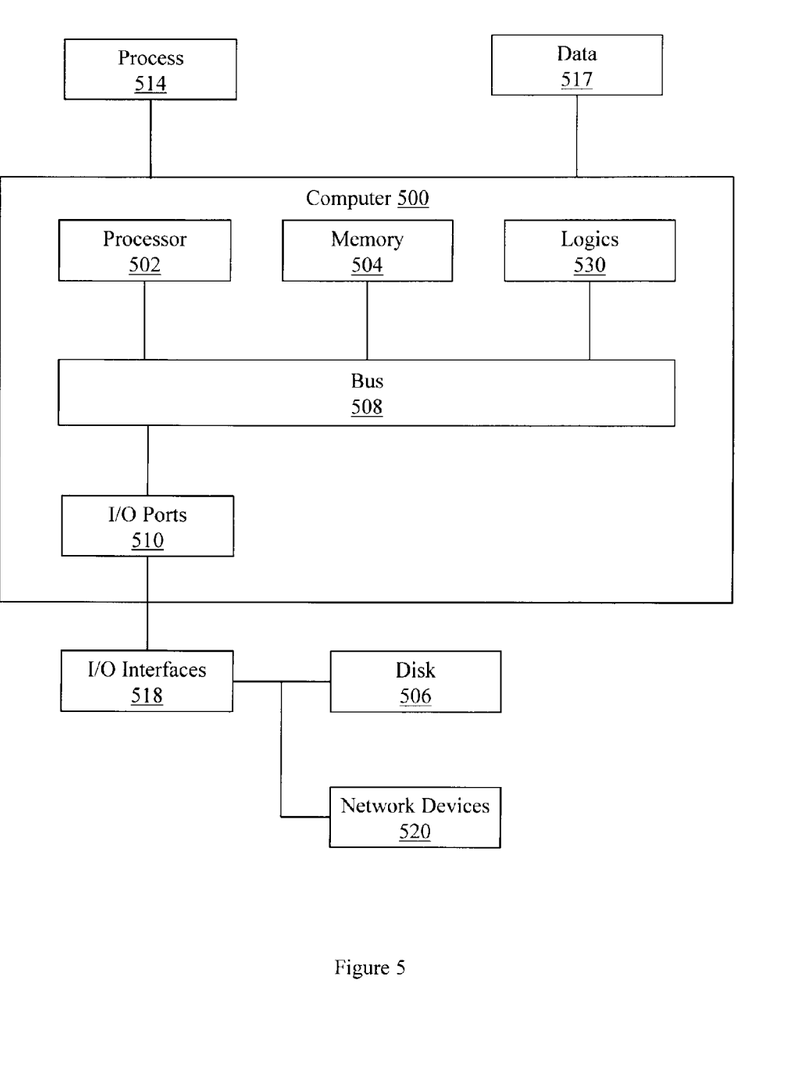
FIG. 5 illustrates an example computer in which example methods illustrated herein can operate.

FIG. 5 illustrates an example computer 500 in which example methods illustrated herein can operate and in which example logics may be implemented. In different examples computer 500 may be part of a digital slide scanner or may be operably connectable to a digital slide scanner configured to scan tissue microarrays.

Computer 500 includes a processor 502, a memory 504, and input/output ports 510 operably connected by a bus 508. In one example, computer 500 may include a set of logics 530 that is configured to perform a method of associating cell orientation disorder with malignancy and risk of post-surgical biochemical recurrence in a CaP patient. In another example, the set of logics 530 may control the computer 500 to compute a BCR score for a cancer patient. Thus, the set of logics 530, whether implemented in computer 500 as hardware, firmware, software, and/or a combination thereof may provide means (e.g., hardware, software, circuit) for receiving digitized image data, means (e.g., hardware, software, circuit) for performing a method of associating cell orientation disorder with malignancy and risk of post-surgical biochemical recurrence in a CaP patient and means (e.g., hardware, software, circuit) for computing a BCR score for a cancer patient. In different examples, the set of logics 530 may be permanently and/or removably attached to computer 500.

Processor 502 can be a variety of various processors including dual microprocessor and other multi-processor architectures. Memory 504 can include volatile memory and/or non-volatile memory. A disk 506 may be operably connected to computer 500 via, for example, an input/output interface (e.g., card, device) 518 and an input/output port 510. Disk 506 may include, but is not limited to, devices like a magnetic disk drive, a tape drive, a Zip drive, a flash memory card, and/or a memory stick. Furthermore, disk 506 may include optical drives like a CD-ROM and/or a digital video ROM drive (DVD ROM). Memory 504 can store processes 514 and/or data 516, for example. Disk 506 and/or memory 504 can store an operating system that controls and allocates resources of computer 500.

Bus 508 can be a single internal bus interconnect architecture and/or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet).

Computer 500 may interact with input/output devices via I/O interfaces 518 and input/output ports 510. Input/output devices can include, but are not limited to, digital slide scanners configured to scan TMAs, digital whole slide scanners, a keyboard, a microscope, a microphone, a pointing and selection device, cameras, video cards, displays, disk 506, network devices 520, and other devices. Input/output ports 510 can include but are not limited to, serial ports, parallel ports, and USB ports.

Computer 500 may operate in a network environment and thus may be connected to network devices 520 via I/O interfaces 518, and/or I/O ports 510. Through the network devices 520, computer 500 may interact with a network. Through the network, computer 500 may be logically connected to remote computers. The networks with which computer 500 may interact include, but are not limited to, a local area network (LAN), a wide area network (WAN), and other networks.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, and method 300. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, (e.g., the data store may store only A, only B, only C, A&B, A&C, B&C, A&B&C, A&A&A, A&A&B, A&A&B&B, A&A&B&B&C, A&A&B&B&C&C). It is not intended to require one of A, one of B, and one of C. When the applicants intend to indicate "at least one of A, at least one of B, and at least one of C", then the phrasing "at least one of A, at least one of B, and at least one of C" will be employed.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer cause the computer to perform a method of associating cellular nuclei orientation entropy with malignancy and risk of post-surgical biochemical recurrence (BCR) in a prostate cancer (CaP) patient, the method comprising:
accessing a tissue microarray core image (TMA) of a section of a prostate demonstrating pathology associated with CaP in the patient;
detecting a cell in a region of interest on the TMA core image;
segmenting the boundary of the cell into a set of cell boundary points;
calculating a direction of the cell as a function of the set of cell boundary points;
constructing a subgraph of a localized cell network within the region of interest by linking individual cells located proximal to each other, where the nodes of the subgraph represent individual cell nuclei centroids, and where the edges of the subgraph are defined between pairs of cells by a probabilistic decaying function;
constructing a cellular orientation co-occurrence matrix, where elements of the cellular orientation co-occurrence matrix comprise cell direction pairs, where the cell direction pairs are defined by the subgraph, and where the cellular orientation co-occurrence matrix aggregates co-occurring cell directions as a function of the frequency with which orientations of two individual cells located proximal to each other co-occur;
deriving second-order statistics of cell orientations in the localized cell network;
selectively differentiating a cancerous tissue region from a non-cancerous tissue region in the image based, at least in part, on the second-order statistics; and
establishing a BCR score for the patient based, at least in part, on the second-order statistics.

2. The non-transitory computer-readable storage medium of claim 1, where detecting the cell and segmenting the boundary of the cell is based on an energy functional of an active contour.

3. The non-transitory computer-readable storage medium of claim 2, the method comprising controlling the computer to:
incorporate a shape prior in a level set formulation, where the shape prior is modeled on the object of interest, where the object of interest is a prostate cell nuclei;
initialize the level set formulation automatically, where initialization is based on a watershed transform, and where the energy functional of an active contour comprises:
a prior shape term, where the prior shape term is modeled on a cell nuclei, and where the prior shape term constrains deformation achieved by the active contour;
a boundary-based term, where the boundary-based term detects nuclei boundaries from image gradients; and
a region term, where the region term drives the shape prior and contour towards the nuclear boundary based on region statistics.

4. The non-transitory computer-readable storage medium of claim 3, the method comprising controlling the computer to combine the prior shape term and the boundary-based term to form a shape plus boundary force expressed in the energy functional of an active contour, where the shape plus boundary force is described by $\beta_s \int_\Omega (\phi)(x) - \psi(x)^2 |\nabla \phi| \delta(\phi) dx$, where $\beta_s > 0$ is an arbitrary positive constant that balances contributions of the boundary based shape prior term, where $\{\phi\}$ is a level set function, where $\psi$ is the shape prior, where $\delta(\cdot)$ is the Dirac delta function, where $\delta(\phi)$ is the contour measure on $\{\phi=0\}$, and where $\Omega$ is a bounded open set in $\mathbb{R}^2$.

5. The non-transitory computer-readable storage medium of claim 3, where the region term is expressed in the energy functional of an active contour as a region force, where the region force is expressed as $\beta_r \int_\Omega \Theta_{in} H_\psi dx + \int_\Omega \Theta_{out} H_{-\psi} dx$, where $\beta_r > 0$ is an arbitrary positive constant that balances contributions of the region term, where $\psi$ is the shape prior, where H(•) is the Heaviside function, where $\Theta_r = |I - u_r|^2 + \mu |\nabla u_r|^2$, where $r \in \{in, out\}$, where $u_r$ such that $r \in \{in, out\}$ are partitioned foreground and background regions, and where $\Omega$ is a bounded open set in $\mathbb{R}^2$.

6. The non-transitory computer-readable storage medium of claim 1, the method comprising obtaining the dominant orientation of the cell through principal component analysis (PCA) of the set of cell boundary points, where the first principal component describes the directionality of the cell in the form of the major axis, and where the greatest variance in the cell boundary occurs along the major axis.

7. The non-transitory computer-readable storage medium of claim 6, the method comprising converting the major axis to an angle counterclockwise from a positive horizontal axis.

8. The non-transitory computer-readable storage medium of claim 1, where the subgraph is a sparsified graph, where the sparsified graph defines a pairwise spatial relationship between cells, and where the contributions of the stromal regions are minimized by preventing the sparsified graph edges from traversing heterogeneous tissues including stroma and epithelium.

9. The non-transitory computer-readable storage medium of claim 1, where the probabilistic decaying function is a probabilistic decaying function of the Euclidean distance between cell centroids.

10. The non-transitory computer-readable storage medium of claim 1, where the density of the subgraph is controlled by a randomly generated value $\alpha$ from 0 through infinity, where 0 represents a high probability of connecting nodes, and infinity represents a low probability of connecting nodes, $\alpha$ being a real number.

11. The non-transitory computer-readable storage medium of claim 1, the method comprising discretizing cell orientations.

12. The non-transitory computer-readable storage medium of claim 1, where the second-order statistics include entropy, homogeneity, energy, correlation, contrast energy, contrast inverse moment, contrast average, contrast variance, contrast entropy, intensity average, intensity variance, or intensity entropy.

13. The non-transitory computer-readable storage medium of claim 1, the method comprising differentiating the cancerous tissue region and the non-cancerous tissue region as a function of the disorganization of the cell orientation, where a level of disorganization below a disorganization threshold indicates a non-cancerous tissue region and where a disorganization above the disorganization threshold indicates a cancerous tissue region.

14. The non-transitory computer-readable storage medium of claim 1, the method comprising summing the co-occurrence matrices to provide a visual interpretation of cell orientation disorder, where the brightness of a co-occurrence value varies directly with co-occurrence of nuclei of differing orientations.

15. A method for controlling a computer to provide a biochemical recurrence (BCR) score for a cancer patient, comprising:
    detecting a cell in a region of interest of a tissue microarray core image (TMA) associated with the cancer patient;
    segmenting cell boundaries of the cell into a set of cell boundaries;
    calculating a cell direction of the cell based, at least in part, on members of the set of cell boundaries;
    constructing a localized subgraph of a cell network in the region of interest of the TMA core by linking cells detected in the region of interest and located proximal to each other, where the nodes of the subgraph represent individual cell nuclei centroids;
    defining pairwise spatial relationships between two or more cells in the subgraph;
    constructing a cell direction co-occurrence matrix based, at least in part, on the pairwise spatial relationships;
    deriving second order statistical features from the cell direction co-occurrence matrix; and
    computing the BCR recurrence score based, at least in part, on the second order statistical features.

16. The method of claim 15, comprising:
    detecting the cell and segmenting the cell boundaries using an energy functional of an active contour, where the energy functional is comprised of a prior shape term, a boundary-based term, and a region term.

17. The method of claim 15, comprising calculating the cell direction from a principal component analysis (PCA) of the set of cell boundaries.

18. The method of claim 15, where the localized subgraph is a cluster graph, and where the nodes of the localized subgraph represent cell centroids.

19. The method of claim 15, where the edges of the localized subgraph between at least one pair of cells are defined by a probabilistic decaying function, where the probabilistic decaying function minimizes the contributions of the stromal regions by preventing subgraph edges from traversing heterogeneous tissues including stroma and epithelium.

20. The method of claim 15, where the second order statistical features include entropy, contrast, energy, or correlation.

21. The method of claim 20, where entropy is defined as $\Sigma_{a,b} -C(a,b) \log(C(a,b))$, where a is a direction of a first cell in a pair of cells, where the pair of cells is in the localized subgraph, where b is a direction of a second cell in the pair of cells, and where C is the cell direction co-occurrence matrix, where the cell direction co-occurrence matrix is a N×N co-occurrence matrix, N being an integer.

22. The method of claim 20, where contrast is defined as $\Sigma_{a,b} |a-b|^2 C(a,b)$, where a is a direction of a first cell in a pair of cells, where the pair of cells is in the localized subgraph, where b is a direction of a second cell in the pair of cells, and where C is the cell direction co-occurrence matrix, where the cell direction co-occurrence matrix is a N×N co-occurrence matrix, N being an integer.

23. The method of claim 20, where energy is defined as $\Sigma_{a,b} C(a,b)^2$, where a is a direction of a first cell in a pair of cells, where the pair of cells is in the localized subgraph, where b is a direction of a second cell in the pair of cells, and where C is the cell direction co-occurrence matrix, where the cell direction co-occurrence matrix is a N×N co-occurrence matrix, N being an integer.

24. The method of claim 20, where correlation is defined as $$\sum_{a,b} \frac{(a - \mu a)(b - \mu b) C(a,b)}{\sigma_a, \sigma_b},$$

where a is a direction of a first cell in a pair of cells, where the pair of cells is in the localized subgraph, where b is a direction of a second cell in the pair of cells, and where C is the cell direction co-occurrence matrix, where the cell direction co-occurrence matrix is a N×N co-occurrence matrix, N being an integer.

25. An apparatus, comprising:
- a processor;
- a memory;
- an input/output interface;
- a set of logics that associate directional disorder with a risk of biochemical recurrence (BCR) in a region of interest in cancerous tissue, and
- an interface to connect the processor, the memory, the input/output interface and the set of logics,
- the set of logics comprising:
  - a first logic that detects a cell in the region of interest, segments boundaries of the cell, and calculates a direction for the cell, where the direction indicates the dominant orientation of the cell;
  - a second logic that constructs a sparsified localized subgraph from detected cells, defines pairwise spatial relationships between cells in the subgraph, and constructs a directional co-occurrence matrix based, at least in part on the pairwise spatial relationships, where the nodes of the sparsified localized subgraph represent the nuclear centroids of the cells; and
  - a third logic that derives a cell orientation entropy (COrE) feature from the directional co-occurrence matrix, and produces a BCR score based, at least in part, on the COrE feature, the COrE feature being entropy, energy, correlation, or contrast.

\* \* \* \* \*